US00PP14227P39

(12) United States Plant Patent
Kerley

(10) Patent No.: US PP14,227 P3
(45) Date of Patent: Oct. 14, 2003

(54) PETUNIA PLANT NAMED 'KERMAR'

(50) Latin Name: *Petunia×hybrida*
Varietal Denomination: Kermar

(76) Inventor: Priscilla G. Kerley, Bethany, 49 Station Road, Over, Cambridge, CB4 5NJ (GB)

( * ) Notice: Subject to any disclaimer, the term of this patent is extended or adjusted under 35 U.S.C. 154(b) by 0 days.

(21) Appl. No.: 10/051,914

(22) Filed: Jan. 17, 2002

(65) Prior Publication Data

US 2003/0135905 P1 Jul. 17, 2003

(51) Int. Cl.[7] ..... A01H 5/00

(52) U.S. Cl. ..... Plt./356

(58) Field of Search ..... Plt./356

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Petunia plant named 'Kermar', characterized by its outwardly spreading, cascading and uniform plant habit; compact growth habit; early flowering habit; and numerous double flowers that are white in color with distinct purple-colored venation.

2 Drawing Sheets

Botanical classification/cultivar designation: Petunia×hybrida cultivar Kermar.

BACKGROUND OF THE INVENTION

The present Invention relates to a new and distinct cultivar of Petunia plant, botanically known as Petunia×hybrida, and hereinafter referred to by the cultivar name Kermar.

The new Petunia is a product of a planned breeding program conducted by the Inventor in Over, Cambridge, United Kingdom. The objective of the breeding program is to create new cascading Petunias with numerous double flowers with attractive flower colors.

The new Petunia originated from a cross made by the Inventor in August, 1998 of the Petunia cultivar Sunsolos, not patented,, as the female, or seed, parent with an unidentified proprietary seedling selection of Petunia with purple-colored flowers, not patented, as the male, or pollen, parent. The new Petunia was selected as a single plant from the resulting progeny in July, 1999 in Over, Cambridge, United Kingdom on the basis of its double and numerous white-colored flowers with distinct purple-colored venation.

Asexual reproduction of the new cultivar by terminal vegetative cuttings since August, 1999, taken in Over, Cambridge, United Kingdom has shown that the unique features of this new Petunia are stable and reproduced true to type in successive generations.

SUMMARY OF THE INVENTION

Plants of the cultivar Kermar have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Kermar'. These characteristics in combination distinguish 'Kermar' as a new and distinct cultivar:

1. Outwardly spreading, cascading and uniform plant habit.

2. Compact growth habit.

3. Early flowering habit.

4. Numerous double flowers that are white in color with distinct purple-colored venation.

Plants of the new Petunia differ from plants of the female parent, the cultivar Sunsolos, in the following characteristics:

1. Plants of the new Petunia are more compact and not as pendulous as plants of the cultivar Sunsolos.

2. Plants of the new Petunia have larger flowers than plants of the cultivar Sunsolos.

3. Plants of the new Petunia have double flowers whereas plants of the cultivar Sunsolos have single flowers.

Plants of the new Petunia differ from plants of the male parent, an unidentified purple-colored double-flowered Petunia selection, in the following characteristics:

1. Flowers of plants of the new Petunia are white in color whereas flowers of plants of the male parent are purple in color.

2. Flowers of plants of the new Petunia have distinct venation whereas flowers of plants of the male parent do not have distinct venation.

Plants of the new Petunia can be compared to plants of the cultivar Silk Road, disclosed in U.S. Plant patent application Ser. No. 09/450,095. In side-by-side comparisons conducted in Over, Cambridge, United Kingdom, plants of the new Petunia differed from plants of the cultivar Silk Road in the following characteristics:

1. Plants of the new Petunia had rounder leaves than plants of the cultivar Silk Road.

2. Plants of the new Petunia flowered about 12 days earlier than plants of the cultivar Silk Road.

3. Plants of the new Petunia had larger flowers than plants of the cultivar Silk Road.

4. Flowers of plants of the new Petunia had fewer petaloids than flowers of plants of the cultivar Silk Road.

Plants of the new Petunia can also be compared to plants of the cultivar Doubloon white Star, not patented. In side-by-side comparisons conducted in Over, Cambridge, United Kingdom, plants of the new Petunia differed from plants of the cultivar Doubloon White Star in the following characteristics:

1. Plants of the new Petunia were more compact than plants of the cultivar Doubloon White Star.

2. Plants of the new Petunia had rounder leaves than plants of the cultivar Doubloon White Star.

3. Plants of the new Petunia flowered about three days earlier than plants of the cultivar Doubloon White Star.

4. Flowers of plants of the new Petunia had fewer petaloids than flowers of plants of the cultivar Doubloon White Star.

BRIEF DESCRIPTION OF THE PHOTOGRAPHS

The accompanying colored photographs illustrate the overall appearance of the new Petunia, showing the colors as true as it is reasonably possible to obtain in colored reproductions of this type. Colors in the photographs may differ slightly from the color values cited in the detailed botanical description which accurately describe the colors of the new Petunia.

The photograph on the first sheet comprises a side perspective view of a typical flowering plant of 'Kermar' grown in a 20-cm hanging basket container.

The photograph on the second sheet comprises a close-up view of typical flowers of 'Kermar'. Plants used in the photographs were about 14 weeks from planting.

DETAILED BOTANICAL DESCRIPTION

The aforementioned photographs and following observations and measurements describe plants grown in Over, Cambridge, United Kingdom, in a plastic-covered greenhouse during the late summer and autumn with day temperatures ranging from 18 to 30° C. and night temperatures ranging from 14 to 20° C. After planting rooted cuttings, plants were pinched one time. Plants used for the description were about 18 weeks from planting. Color references are made to The Royal Horticultural Society Colour Chart, 1995 edition, except where general terms of ordinary dictionary significance are used.

Botanical classification: Petunia×hybrida cultivar Kermar.

Parentage:

*Female parent.*—Petunia×hybrida cultivar Sunsolos, not patented.

*Male parent.*—Unidentified proprietary seedling selection of Petunia×hybrida, not patented.

Propagation:

*Type cutting.*—Terminal vegetative cuttings.

*Time to initiate roots.*—Summer: About 10 days at 21° C. Winter: About 14 days at 21° C.

*Time to produce a rooted young plant.*—Summer: About 30 days at 20° C. Winter: About 45 days at 20° C.

*Root description.*—Fine, fibrous.

*Rooting habit.*—Freely branching.

Plant description:

*Form.*—Annual flowering plant; indeterminate; initially upright, then outwardly spreading and cascading; uniform; compact growth habit. Freely branching habit with about seven lateral branches developing after pinching (removal of terminal apices).

*Plant height.*—About 16 cm.

*Plant diameter.*—About 60 cm.

*Vigor.*—Moderately vigorous.

*Lateral branches.*—Length: About 36.5 cm. Diameter: About 3.5 mm. Internode length: About 2.4 cm. Texture: Pubescent. Color: 144A to 146B; younger branches overlain with 187A.

*Foliage description.*—Arrangement: Alternate before flowering; opposite after flowers develop; simple. Length: About 5.3 cm. Width: About 3.2 cm. Shape: Rounded. Apex: Slightly acute. Base: Slightly acute to slightly obtuse. Margin. Entire; pubescent. Texture: Upper surface: Slightly pubescent. Lower surface: Pubescence along veins. Venation pattern: Pinnate, arcuate. Color: Developing leaves, upper surface: 137B. Developing leaves, lower surface: 137C. Fully expanded leaves, upper surface: 137B. Fully expanded leaves, lower surface: 137C to 137D. Venation, upper surface: 137B. Venation, lower surface: 137C to 137D. Petiole length: About 1.1 cm. Petiole diameter: About 2.4 mm. Petiole color: 146B.

Flower description:

*Flower type and habit.*—Double salverform flowers; flowers face mostly upward or outward; axillary. Very freely flowering habit, typically one flower per node; indeterminate.

*Natural flowering season.*—Long day responsive; long flowering period, spring until frost in the autumn; flowering continuous during this period. Plants start flowering about 42 days after planting rooted cuttings. Flowers persistent.

*Flower longevity on the plant.*—About three days.

*Fragrance.*—Faint, sweet.

*Flower size.*—Diameter: About 6.5 cm. Tube length: About 1.9 cm. Throat diameter, distal end: About 1.5 cm. Tube diameter, proximal end: About 3.5 to 5 mm.

*Flower buds* (*at stage of showing color*).—Length: About 2.1 cm. Diameter: About 1.2 cm. Shape: Elongated oblong with ruffled apices. Color: 144A with varying amounts of veining, 78A to 78B; towards the apices, 144A flushed with 78D.

*Corolla.*—Quantity/arrangement: About five fused outer petals in a single whorl, funnel form; interior to the outer whorl, about five progressively smaller petaloids, variable in size. Petal length from throat: About 3 cm. Petal width: About 3 cm. Petal/petaloid shape: Roughly spatulate. Petal/petaloid apex: Cuspidate; slightly incurved. Petal/petaloid margin: Entire; ruffled. Petal/petaloid texture: Smooth, velvety. Color: Petals/petaloids, upper surface, when opening and fully opened: 155A. Petals/petaloids, lower surface, when opening and fully opened: 155C flushed with 83D. Flower throat (inside): 155A. Flower tube (outside): 144D flushed with 78B; veins, 144A, flushed with 79C. Venation, upper petal/petaloid surface: 83A. Venation, lower petal/petaloid surface: Main veins, 148A or 200C; smaller veins, 83D. Venation, throat: Close to 187A. Venation, tube: Close to 187A.

*Sepals.*—Arrangement/appearance: Single whorl of five sepals fused at base, star-shaped. Length: About 1.1 cm. Width: About 2.9 mm. Shape: Strap-like;

elongate. Apex: Blunt, rounded. Margin: Entire, pubescent. Texture, both surfaces: Pubescent, glandular. Color: Upper surface: 137B. Lower surface: 137D.

*Peduncles.*—Length: About 2.75 cm. Width: About 2.1 mm. Angle: About 60 to 70° from the stem. Strength: Strong. Texture: Pubescent. Color: 137D overlain with 165A.

*Reproductive organs.*—Stamens: Quantity per flower: About four or five. Stamen length: About 2.4 cm. Anther shape: Ovoid. Anther size: Length: About 1 mm. Width: About 1.5 mm. Anther color: Pale gray blue, closest to 115D. Pollen amount: Moderate. Pollen color: 106B. Pistils: Quantity per flower: One or none, typically distorted. Style length: About 5 mm. Style color: 141D. Stigma shape: Four-parted, rounded. Stigma color: 144B to 144C. Ovary color: 141D.

*Seed/fruit.*—Seed and/or fruit production has not been observed to date.

Disease/pest resistance: Plants of the new Petunia have not been noted to be resistant to pathogens or pests common to Petunia.

Garden performance: Plants of the new Petunia have been observed to have good garden performance. Plants of the new Petunia have been noted to tolerate temperatures from 0 to 35° C. and have good tolerance to rain and wind.

It is claimed:

1. A new and distinct cultivar of Petunia plant named 'Kermar', as illustrated and described.

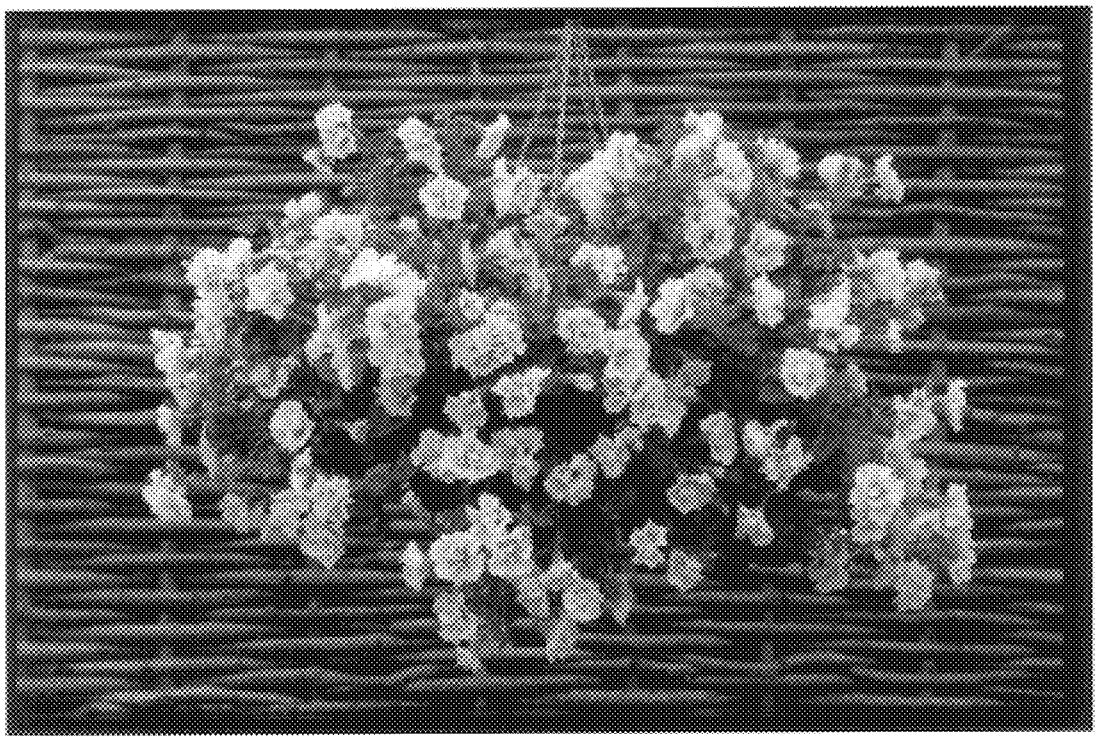

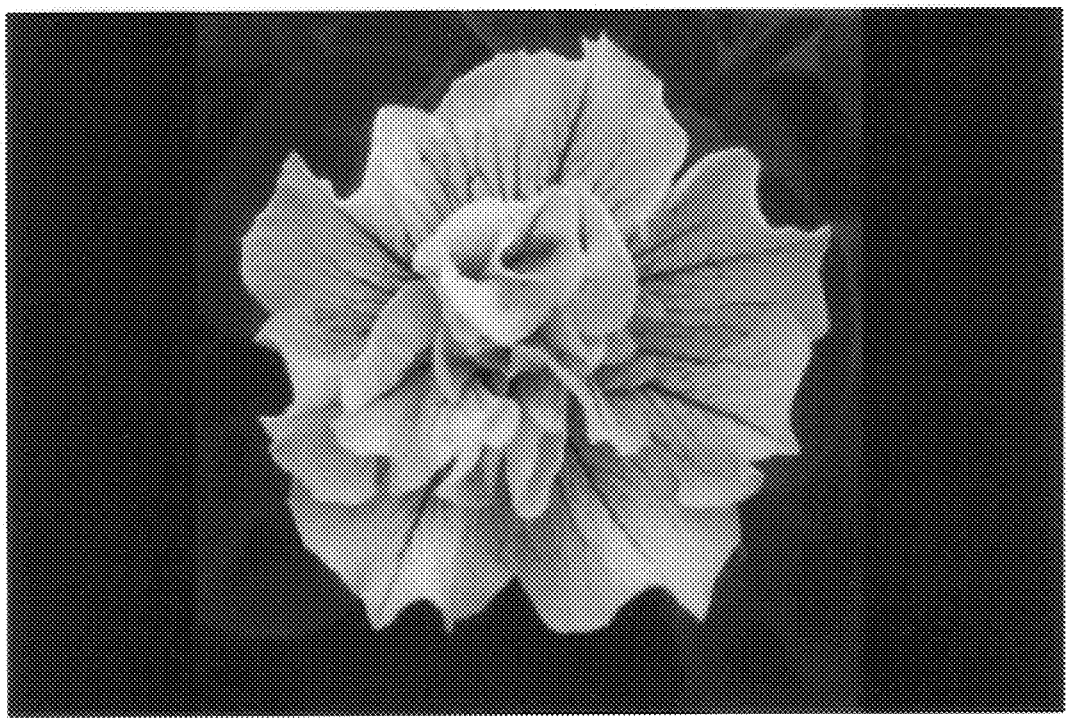

* * * * *